United States Patent
Lim et al.

(10) Patent No.: US 11,431,028 B2
(45) Date of Patent: Aug. 30, 2022

(54) NON-AQUEOUS ELECTROLYTE SOLUTION FOR LITHIUM SECONDARY BATTERY AND LITHIUM SECONDARY BATTERY INCLUDING THE SAME

(71) Applicant: LG Chem, Ltd., Seoul (KR)

(72) Inventors: Young Min Lim, Daejeon (KR); Kyung Mi Lee, Daejeon (KR); Chul Haeng Lee, Daejeon (KR)

(73) Assignee: LG Energy Solution, Ltd.

( * ) Notice: Subject to any disclaimer, the term of this patent is extended or adjusted under 35 U.S.C. 154(b) by 358 days.

(21) Appl. No.: 16/635,076

(22) PCT Filed: Nov. 22, 2018

(86) PCT No.: PCT/KR2018/014470
§ 371 (c)(1),
(2) Date: Jan. 29, 2020

(87) PCT Pub. No.: WO2019/103496
PCT Pub. Date: May 31, 2019

(65) Prior Publication Data
US 2020/0251777 A1  Aug. 6, 2020

(30) Foreign Application Priority Data

Nov. 22, 2017  (KR) .................. 10-2017-0156345
Nov. 22, 2018  (KR) .................. 10-2018-0145685

(51) Int. Cl.
*H01M 10/0567* (2010.01)
*H01M 10/0525* (2010.01)
*H01M 10/0569* (2010.01)
*C07D 233/60* (2006.01)

(52) U.S. Cl.
CPC ...... *H01M 10/0567* (2013.01); *C07D 233/60* (2013.01); *H01M 10/0525* (2013.01); *H01M 10/0569* (2013.01); *H01M 2300/0025* (2013.01)

(58) Field of Classification Search
None
See application file for complete search history.

(56) References Cited

U.S. PATENT DOCUMENTS

| | | | |
|---|---|---|---|
| 2010/0143805 A1 | 6/2010 | Hintermann et al. | |
| 2011/0045361 A1 | 2/2011 | Abe et al. | |
| 2011/0159377 A1 | 6/2011 | Lee et al. | |
| 2018/0358655 A1* | 12/2018 | Kono | H01G 11/22 |
| 2020/0044287 A1 | 2/2020 | Kim et al. | |

FOREIGN PATENT DOCUMENTS

| | | |
|---|---|---|
| CN | 101345325 A | 1/2009 |
| CN | 106099181 A | 11/2016 |
| EP | 3518334 A1 | 7/2019 |
| JP | 3911870 B2 | 5/2007 |
| JP | 20166759 A | 1/2016 |
| JP | 2016139567 A | 8/2016 |
| JP | 2016192381 A | 11/2016 |
| JP | 2017108127 A | 6/2017 |
| KR | 20090080868 A | 7/2009 |
| KR | 20100015432 A | 2/2010 |
| KR | 20100138988 A | 12/2010 |
| WO | 2008153296 A1 | 12/2008 |
| WO | 2015111612 A1 | 7/2015 |
| WO | 2016158986 A1 | 10/2016 |

OTHER PUBLICATIONS

Extended European Search Report for Application No. 18881105.3 dated Jul. 14, 2020, 8 pages.
International Search Report from Application No. PCT/KR2018/014470 dated Mar. 4, 2019, 2 pages.

* cited by examiner

*Primary Examiner* — Carlos Barcena
(74) *Attorney, Agent, or Firm* — Lerner, David, Littenberg, Krumholz & Mentlik, LLP

(57) ABSTRACT

A non-aqueous electrolyte solution for a lithium secondary battery, and a lithium secondary battery including the same are disclosed herein. In some embodiments, a non-aqueous electrolyte solution includes a lithium salt, a non-aqueous solvent including a carbonate-based solvent and propyl propionate, and a compound represented by Formula 1. In some embodiments, the carbonate-based solvent is ethylene carbonate.

9 Claims, 1 Drawing Sheet

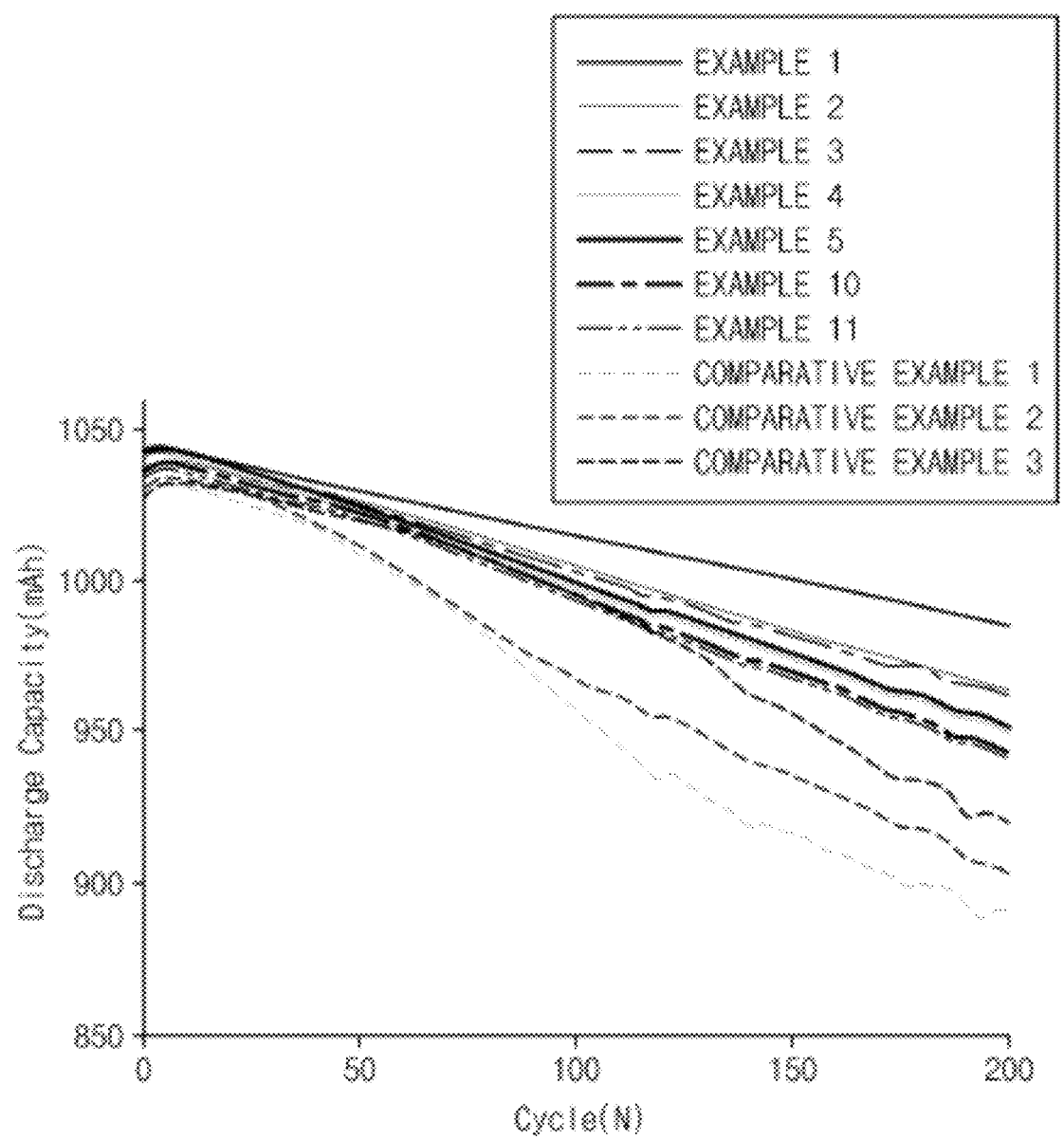

NON-AQUEOUS ELECTROLYTE SOLUTION FOR LITHIUM SECONDARY BATTERY AND LITHIUM SECONDARY BATTERY INCLUDING THE SAME

CROSS-REFERENCE TO RELATED APPLICATIONS

This application is a national phase entry under 35 U.S.C. § 371 of International Application No. PCT/KR2018/014470, filed on Nov. 22, 2018, which claims priority from Korean Patent Application Nos. 10-2017-0156345, filed on Nov. 22, 2017, and 10-2018-0145685, filed on Nov. 22, 2018, the disclosures of which are incorporated by reference herein.

TECHNICAL FIELD

The present invention relates to a non-aqueous electrolyte solution for a lithium secondary battery which may suppress gas generation and a lithium secondary battery including the same.

BACKGROUND ART

In line with miniaturization, lightweight, thin profile, and portable trends in electronic devices according to the development of information and telecommunications industry, the need for high energy density lithium secondary batteries used as power sources of such electronic devices has increased.

Lithium secondary batteries, specifically, lithium ion batteries (LIB), as batteries that may best meet the need, have been adopted as power sources of many portable devices due to high energy density and ease of design.

Recently, a lithium secondary battery, which may maintain excellent performance not only at room temperature but also in a more severe outside environment such as a high-temperature or low-temperature environment, is required as the range of the lithium secondary batteries used has expanded from conventional small electronic devices to large electronic devices, cars, or smart grids.

A lithium secondary battery currently used is composed of a carbon-based negative electrode capable of intercalating and deintercalating lithium ions, a positive electrode formed of lithium-containing transition metal oxide, and a non-aqueous electrolyte solution in which an appropriate amount of a lithium salt is dissolved in a mixed carbonate-based non-aqueous organic solvent, wherein charge and discharge may be possible while a phenomenon is repeated in which lithium ions, which are deintercalated from the positive electrode by charging, are intercalated into the carbon-based negative electrode and again deintercalated during discharging.

An increase in driving voltage of the lithium secondary battery is the most efficient and easy method among methods for achieving a high capacity and high output lithium secondary battery.

However, since a reaction of an electrolyte with an electrode active material is increased when the driving voltage is increased, thermal durability is reduced at high temperatures and a large amount of gas is generated, and thus, there is a limitation in that a cell swelling phenomenon occurs. This phenomenon is particularly severe when the driving voltage of the battery is a high voltage of 4.35 V or more.

Thus, in order to develop a high capacity and high output lithium secondary battery, there is a need to develop a technique capable of effectively controlling an interfacial reaction of the electrolyte solution and the electrode even at a high driving voltage.

PRIOR ART DOCUMENT

Japanese Patent No. 3911870

DISCLOSURE OF THE INVENTION

Technical Problem

An aspect of the present invention provides a non-aqueous electrolyte solution for a lithium secondary battery which may effectively suppress gas generation by forming a stable ion conductive film on the surface of a negative electrode.

Another aspect of the present invention provides a lithium secondary battery in which cell swelling is low by including the above-described non-aqueous electrolyte solution for a lithium secondary battery.

TECHNICAL SOLUTION

According to an aspect of the present invention, there is provided a non-aqueous electrolyte solution for a lithium secondary battery including:
a lithium salt,
a non-aqueous solvent including a carbonate-based solvent and propyl propionate, and
a compound represented by Formula 1 below.

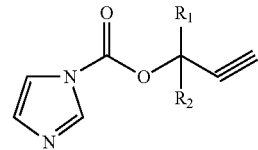

[Formula 1]

In Formula 1,
$R_1$ and $R_2$ are each independently hydrogen or a substituted or unsubstituted alkyl group having 1 to 6 carbon atoms.

The non-aqueous solvent may include the carbonate-based solvent and the propyl propionate in a weight ratio of 2:8 to 4:6.

The carbonate-based solvent may include ethylene carbonate.

Also, the non-aqueous solvent may further include ethyl propionate.

Furthermore, the compound represented by Formula 1 may be selected from the group consisting of compounds represented by Formulae 1a to 1c below.

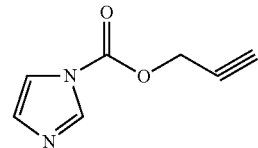

[Formula 1a]

-continued

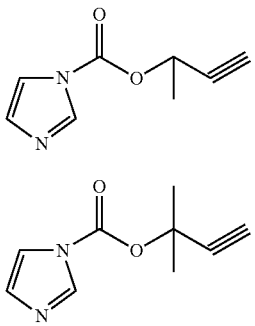

[Formula 1b]

[Formula 1c]

Specifically, the compound represented by Formula 1 may be selected from the group consisting of the compounds represented by Formulae 1b and 1c.

The compound represented by Formula 1 may be included in an amount of 0.01 wt % to 11.5 wt %, for example, 0.1 wt % to 10 wt % based on a total weight of the non-aqueous electrolyte solution.

According to another aspect of the present invention, there is provided a lithium secondary battery including the non-aqueous electrolyte solution for a lithium secondary battery of the present invention.

ADVANTAGEOUS EFFECTS

According to the present invention, a non-aqueous electrolyte solution for a lithium secondary battery may suppress gas generation and cell swelling during operation at a high voltage of 4.35 V or more and during high-temperature storage by using propyl propionate, as a non-aqueous solvent, in an amount of 60 wt % to 80 wt % to reduce an amount of a carbonate-based solvent used which is sensitive to side reactions. Also, since the non-aqueous electrolyte solution for a lithium secondary battery of the present invention may form a stable ion conductive film on the surface of a negative electrode by including a compound containing both of a propargyl group known to have metal ion adsorbability and an imidazole group effective for solid electrolyte interface (SEI) formation as an additive, gas generation due to a side reaction between a positive electrode and an electrolyte may be suppressed, and thus, the cell swelling may be significantly reduced.

BRIEF DESCRIPTION OF THE DRAWINGS

The following drawings attached to the specification illustrate preferred examples of the present invention by example, and serve to enable technical concepts of the present invention to be further understood together with detailed description of the invention given below, and therefore the present invention should not be interpreted only with matters in such drawings.

The FIGURE is a graph illustrating the results of cycle life characteristics evaluation of lithium secondary batteries according to Experimental Example 1 of the present invention.

MODE FOR CARRYING OUT THE INVENTION

Hereinafter, the present invention will be described in more detail.

It will be understood that words or terms used in the specification and claims shall not be interpreted as the meaning defined in commonly used dictionaries, and it will be further understood that the words or terms should be interpreted as having a meaning that is consistent with their meaning in the context of the relevant art and the technical idea of the invention, based on the principle that an inventor may properly define the meaning of the words or terms to best explain the invention.

In the present specification, it will be further understood that the terms "include," "comprise," or "have" when used in this specification, specify the presence of stated features, numbers, steps, elements, or combinations thereof, but do not preclude the presence or addition of one or more other features, numbers, steps, elements, or combinations thereof.

In the present specification, the expression denotes wt % unless otherwise indicated explicitly.

Electrolyte for Lithium Secondary Battery

First, a non-aqueous electrolyte solution for a lithium secondary battery according to the present invention will be described.

The non-aqueous electrolyte solution for a lithium secondary battery of the present invention includes:
a lithium salt,
a non-aqueous solvent including a carbonate-based solvent and propyl propionate, and
a compound represented by Formula 1 below.

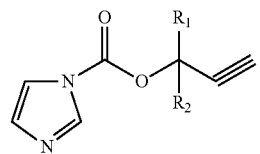

[Formula 1]

In Formula 1,
$R_1$ and $R_2$ are each independently hydrogen or a substituted or unsubstituted alkyl group having 1 to 6 carbon atoms.

(1) Lithium Salt

First, in an electrolyte for a lithium secondary battery according to an embodiment of the present invention, any lithium salt typically used in an electrolyte for a lithium secondary battery may be used as the lithium salt without limitation, and, for example, the lithium salt may include $Li^+$ as a cation, and may include at least one selected from the group consisting of $F^-$, $Cl^-$, $Br^-$, $I^-$, $NO_3^-$, $N(CN)_2^-$, $PF_6^-$, $BF_4^-$, $ClO_4^-$, $AlO_4^-$, $AlCl_4^-$, $SbF_6^-$, $AsF_6^-$, $B_{10}Cl_{10}^-$, $BF_2C_2O_4^-$, $BC_4O_8^-PF_4C_2O_4^-$, $PF_2C_4O_8^-$, $(C_3)_2PF_4^-$, $(CF_3)_3PF_3^-$, $(CF_3)_4PF_2^-$, $(CF_3)_5PF^-$, $(CF_3)_6P^-$, $CF_3SO_3^-$, $C_4F_9SO_3^-$, $CF_3CF_2SO_3^-$, $(CF_3SO_2)_2N^-$, $(FSO_2)_2N^-$, $CF_3CF_2(CF_3)_2CO^-$, $(CF_3SO_2)_2CH^-$, $CH_3SO_3^-$, $CF_3(CF_2)_7SO_3^-$, $CF_3CO_2^-$, $CH_3CO_2^-$, $SCN^-$ and $(CF_3CF_2SO_2)_2N^-$ as an anion. Specifically, the lithium salt may include a single material selected from the group consisting of LiCl, LiBr, $LiClO_4$, $LiPF_6$, $LiBF_4$, $LiB_{10}Cl_{10}$, $LiCF_3CO_2$, $LiCH_3SO_3$, $LiAlCl_4$, and $LiAlO_4$, or a mixture of two or more thereof.

The lithium salt may be appropriately changed in a normally usable range but may be included in a concentration of 0.8 M to 2 M, for example, 1 M to 1.5 M in the electrolyte to obtain an optimum effect of forming a film for preventing corrosion of a surface of an electrode. In a case in which the concentration of the electrolyte salt is greater than 2 M, since viscosity of the electrolyte for a lithium secondary battery is excessively increased, wettability of the electrolyte may be degraded and the effect of forming the film may be reduced. In a case in which the concentration of the lithium salt is less than 0.8 M, since mobility of lithium ions is reduced, capacity characteristics may be degraded.

(2) Non-Aqueous Solvent

The non-aqueous solvent may include a carbonate-based solvent and propyl propionate.

Specifically, the carbonate-based solvent may include at least one solvent selected from the group consisting of a linear carbonate-based solvent and a cyclic carbonate-based solvent, and may specifically include a cyclic carbonate-based solvent.

The linear carbonate-based solvent, as a solvent having low viscosity and low permittivity, may include at least one selected from the group consisting of dimethyl carbonate (DMC), diethyl carbonate (DEC), dipropyl carbonate, ethylmethyl carbonate (EMC), methylpropyl carbonate, and ethylpropyl carbonate.

Also, the cyclic carbonate-based solvent may include at least one selected from the group consisting of ethylene carbonate (EC), propylene carbonate (PC), 1,2-butylene carbonate, 2,3-butylene carbonate, 1,2-pentylene carbonate, 2,3-pentylene carbonate, vinylene carbonate, and fluoroethylene carbonate (FEC).

Specifically, the carbonate-based solvent may include ethylene carbonate having high permittivity. Also, the carbonate-based solvent may include a mixed solvent in which propylene carbonate having a relatively lower melting point than the ethylene carbonate is added to the ethylene carbonate.

In a case in which the mixed solvent of the ethylene carbonate and the propylene carbonate is used as the carbonate-based solvent, a weight ratio of the ethylene carbonate to the propylene carbonate may be in a range of 1:0.2 to 1:1, preferably 1:0.2 to 1:0.8, and more preferably 1:0.3 to 1:0.6.

The weight ratio of the ethylene carbonate to the propylene carbonate may have an important effect on improving both low temperature and room temperature output and capacity characteristics after high-temperature storage during the preparation of the secondary battery, and, in a case in which the weight ratio is within the above range, charge/discharge capacity and life characteristics of the secondary battery may be sufficiently improved.

In a case in which the weight ratio of the propylene carbonate to the ethylene carbonate is greater than 1, since a degree of dissociation of the lithium salt is reduced, ionic conductivity becomes poor and stability of a carbon negative electrode may be reduced. Also, in a case in which the weight ratio of the propylene carbonate to the ethylene carbonate is less than 0.2, the ionic conductivity may be relatively decreased.

Since the carbonate-based solvent is sensitive to side reactions due to high reactivity at a high voltage, gas generation is increased in a case in which a large amount of the carbonate-based solvent is used as the non-aqueous solvent when used in a high voltage battery, and thus, cell swelling is increased and high-temperature storage stability may deteriorate.

Therefore, in the present invention, the gas generation and the cell welling may be suppressed by including an ester-based organic solvent, particularly, propyl propionate having a low melting point and high stability at a high temperature (viscosity at room temperature of about 0.7 cP) as well as the carbonate-based solvent, as the non-aqueous solvent.

The propyl propionate having high high-voltage stability is included in an amount of 60 wt % to 80 wt %, for example, 60 wt % to 70 wt % based on a total weight of the non-aqueous solvent, and, in a case in which the amount of the propyl propionate satisfies the above range, the high-temperature storage stability may be improved by suppressing gas generation and cell swelling at a high voltage of 4.35 V or more and during high-temperature storage at 60° C. or more.

In a case in which the amount of the propyl propionate is greater than 80 wt %, since the amount of the carbonate-based solvent is relatively reduced, the mobility of lithium ions may be reduced to decrease the ionic conductivity and the film forming effect due to the carbonate-based solvent may be reduced to reduce stability of the cell.

Thus, the carbonate-based solvent and the propyl propionate may be included in a weight ratio of 2:8 to 4:6, for example, 3:7 to 4:6.

In a case in which the weight ratio of the propyl propionate to the carbonate-based solvent satisfies the above range, a synergistic effect by the mixed use of the two organic solvents may be achieved. If the weight ratio of the propyl propionate to the carbonate-based solvent is less than 6, the viscosity of the electrolyte may be increased to reduce the wettability of the electrolyte and a high-temperature oxidation reaction of the carbonate-based solvent may be increased to degrade the stability of the cell and swelling performance at a high voltage. Also, the weight ratio of the propyl propionate to the carbonate-based solvent is greater than 8, since it is difficult to form a stable solid electrolyte interface (SEI) passivation layer, the stability of the cell may be reduced.

Also, the non-aqueous solvent may further include a linear ester-based compound in addition to the carbonate-based solvent and the propyl propionate solvent.

The linear ester-based compound may include at least one selected from the group consisting of methyl acetate, ethyl acetate, propyl acetate, methyl propionate, ethyl propionate, and butyl propionate, and may specifically include ethyl propionate.

In a case in which the linear ester-based compound is further included, the propyl propionate and the linear ester-based compound may be included in a weight ratio of 6:4 to 9:1.

In a case in which the weight ratio of the linear ester-based compound to the propyl propionate is greater than 4, the ionic conductivity may be increased, but, since gas generation rate is increased due to the decomposition of the solvent at a high temperature, stability may be reduced.

(3) Compound Represented by Formula 1

The electrolyte of the present invention includes a compound represented by Formula 1 below.

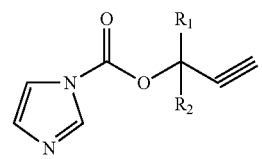

[Formula 1]

In Formula 1, $R_1$ and $R_2$ are each independently hydrogen or a substituted or unsubstituted alkyl group having 1 to 6 carbon atoms.

In general, an SEI affecting a battery reaction is formed on a surface of a negative electrode (graphite) while an electrolyte solution is decomposed before lithium ions discharged from a positive electrode are intercalated into the negative electrode (graphite) during initial charge of a secondary battery. The SEI not only has the property of passing the lithium ions and blocking movement of electrons, but also acts as a protective film that prevents the electrolyte solution from being decomposed continuously. Thus, when the SEI is formed on the surface of the negative electrode, the decomposition of the electrolyte solution due to the movement of the electrons between the electrode and the electrolyte solution is suppressed and only the intercalation and deintercalation of the lithium ions selectively becomes possible.

However, it is difficult to continuously maintain performance of the formed SEI, and the formed SEI is destroyed by shrinkage and expansion due to repeated charge and discharge cycles or by heat and impact from the outside. Charge is additionally or irreversibly consumed while the destroyed SEI is restored by the continuous charge and discharge process so that reversible capacity is continuously reduced. Particularly, since interfacial resistance is increased as a thickness of the solid film formed due to the decomposition of the electrolyte solution is increased, battery performance is degraded.

Furthermore, the dissolution of metallic foreign matter, such as cobalt (Co), manganese (Mn), and nickel (Ni), from a positive electrode active material is increased by structural collapse of the positive electrode active material and a side reaction with the electrolyte solution while an excessive amount of lithium ions is discharged from the positive electrode during overcharge at a high voltage of 4.35 V or more or during high-temperature storage, and the dissolved metallic foreign matter moves to the negative electrode and precipitates as dendrites on the surface of the negative electrode to cause a micro-short circuit between the positive electrode and the negative electrode. Overall performance of the secondary battery is degraded while a low-voltage phenomenon, in which a voltage of the battery is reduced, occurs due to the short circuit. The low-voltage phenomenon may also be caused by metallic foreign matter which is included in raw materials of the lithium battery or incorporated in a process.

However, in the present invention, since an additive capable of forming a stable film on the surfaces of the positive electrode and the negative electrode is included, a lithium secondary battery having improved high-voltage life characteristics and high-temperature storage performance may be prepared by effectively suppressing the decomposition of the electrolyte solution and electrodeposition of the metal dissolved due to the structural collapse of the positive electrode on the negative electrode in a battery at a high voltage of 4.35 V or more.

That is, since the compound represented by Formula 1 includes a propargyl group having a triple bond known to have metal ion adsorbability and an oxygen atom, the propargyl group, which is separated by cleavage of a nitrogen (N) atom and a carbon (C) atom of an imidazole group, may adsorb on the metallic foreign matter, such as iron (Fe), Co, Mn, and Ni, dissolved from the positive electrode during high-voltage charge, and thus, a negative electrode degradation phenomenon, which occurs by the electrodeposition of the metallic foreign matter on the surface of the negative electrode, may be effectively suppressed.

Also, the compound represented by Formula 1 may form a stable ion conductive film on the surface of the negative electrode because the lone pair of the nitrogen (N) atom of the imidazole group is reduced on the surface of the negative electrode by being reacted with alkyl carbonate as a decomposition product of ethylene carbonate (EC) used as the organic solvent. Thus, an additional electrolyte solution decomposition reaction may not only be suppressed during charge and discharge, but cycle life characteristics and high-temperature storage performance may also be improved by facilitating the intercalation and deintercalation of lithium ions into and from the negative electrode even during overcharge or high-temperature storage.

The compound represented by Formula 1 may be selected from the group consisting of compounds represented by Formulae 1a to 1c below.

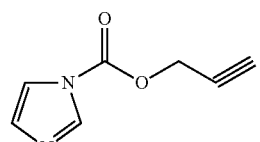

[Formula 1a]

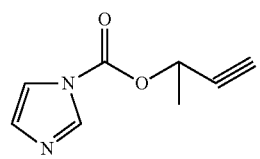

[Formula 1b]

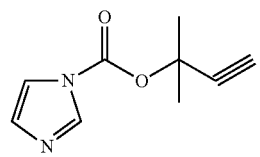

[Formula 1c]

Specifically, the compound represented by Formula 1 may be selected from the group consisting of the compounds represented by Formulae 1b and 1c which may more stably react than the compound represented by Formula 1a, because the compounds represented by Formulae 1b and 1c are substituted with an electron donating group such as a methyl group.

The compound represented by Formula 1 may be included in an amount of 0.01 wt % to 11.5 wt %, particularly 0.1 wt % to 10 wt %, more particularly 0.1 wt % to 7 wt % based on a total amount of the non-aqueous electrolyte solution.

In a case in which the compound represented by Formula 1 is included in an amount within the above range, a secondary battery having more improved overall performance may be prepared. For example, when the amount of the additive is 0.01 wt % or more, an SEI stabilization effect or a metal dissolution suppression effect may be improved, and, when the amount of the additive is 10 wt % or less, the maximum metal dissolution suppression effect may be obtained within an increase in resistance which may be accommodated.

(4) Additive

In order to further improve low-temperature high-rate discharge characteristics, high-temperature stability, overcharge prevention, and an effect of improving swelling during high-temperature storage, the electrolyte for a lithium secondary battery of the present invention may further include an additional additive capable of forming a more stable ion conductive film on the surface of the electrode, if necessary.

Specifically, as a representative example, the additional additive may include at least one additive for forming an SEI which is selected from the group consisting of a sultone-based compound, a sulfate-based compound, a sulfite-based compound, a halogen-substituted carbonate-based compound, a nitrile-based compound, a cyclic carbonate-based compound, a sulfone-based compound, a phosphate-based compound, and a borate-based compound.

The sultone-based compound may include at least one compound selected from the group consisting of 1,3-propane sultone (PS), 1,4-butane sultone, ethane sultone, 1,3-propene sultone (PRS), 1,4-butene sultone, and 1-methyl-1,3-propene sultone, and may be included in an amount of 0.3 wt % to 5 wt %, for example, 1 wt % to 5 wt % based on a total weight of the electrolyte. In a case in which the amount of the sultone-based compound in the electrolyte is greater than 5 wt %, since an excessively thick film is formed on the surface of the electrode, output degradation and the increase in resistance may occur, and, since the resistance may be increased by the excessive amount of the additive in the electrolyte, output characteristics may be degraded.

The sulfate-based compound may include ethylene sulfate (Esa), trimethylene sulfate (TMS), or methyl trimethylene sulfate (MTMS), and may be included in an amount of 3 wt % or less based on the total weight of the electrolyte.

The sulfite-based compound may include at least one compound selected from the group consisting of ethylene sulfite, methyl ethylene sulfite, ethyl ethylene sulfite, 4,5-dimethyl ethylene sulfite, 4,5-diethyl ethylene sulfite, propylene sulfite, 4,5-dimethyl propylene sulfite, 4,5-diethyl propylene sulfite, 4,6-dimethyl propylene sulfite, 4,6-diethyl propylene sulfite, and 1,3-butylene glycol sulfite, and may be included in an amount of 3 wt % or less based on the total weight of the electrolyte.

Also, the halogen-substituted carbonate-based compound may include fluoroethylene carbonate (FEC) and may be included in an amount of 5 wt % or less based on the total weight of the electrolyte. In a case in which the amount of the halogen-substituted carbonate-based compound is greater than 5 wt %, cell swelling performance may deteriorate.

Furthermore, the nitrile-based compound may include at least one compound selected from the group consisting of succinonitrile (NA), adiponitrile (Adn), acetonitrile, propionitrile, butyronitrile, valeronitrile, caprylonitrile, heptanenitrile, cyclopentane carbonitrile, cyclohexane carbonitrile, 2-fluorobenzonitrile, 4-fluorobenzonitrile, difluorobenzonitrile, trifluorobenzonitrile, phenylacetonitrile, 2-fluorophenylacetonitrile, and 4-fluorophenylacetonitrile.

A total weight of the nitrile-based compound may be in a range of 5 wt % to 8 wt %, for example, 6 wt % to 8 wt % based on the total weight of the electrolyte. In a case in which the total weight of the nitrile-based compound in the electrolyte is greater than 8 wt %, since the resistance is increased due to an increase in the film formed on the surface of the electrode, battery performance may deteriorate.

Also, the cyclic carbonate-based compound may include vinylene carbonate (VC) or vinyl ethylene carbonate and may be included in an amount of 3 wt % or less based on the total weight of the electrolyte. In a case in which the amount of the cyclic carbonate-based compound in the electrolyte is greater than 3 wt %, cell swelling inhibition performance may deteriorate.

The sulfone-based compound may include at least one compound selected from the group consisting of divinyl sulfone, dimethyl sulfone, diethyl sulfone, methyl ethyl sulfone, and methyl vinyl sulfone, and may be included in an amount of 3 wt % or less based on the total weight of the electrolyte.

The phosphate-based compound may include at least one compound selected from the group consisting of lithium difluoro bis(oxalato)phosphate, lithium difluoro phosphate, tetramethyltrimethylsilyl phosphate (TMSPa), trimethylsilyl phosphite (TMSPi), tris(2,2,2-trifluoroethyl)phosphate (TFEPa), and tris(trifluoroethyl)phosphite (TFEPi), and may be included in an amount of 3 wt % or less based on the total weight of the electrolyte.

The borate-based compound may include lithium oxalyldifluoroborate and may be included in an amount of 3 wt % or less based on the total weight of the electrolyte.

Two or more of the additives for forming an SEI may be mixed and included, and the additives for forming an SEI may be included in a total amount of 20 wt % or less based on the total weight of the electrolyte. In a case in which the amount of the additives is greater than 20 wt %, since the side reaction in the electrolyte during charge and discharge of the battery may not only excessively occur, but the additives may also not be sufficiently decomposed at high temperatures, it may be present in the form of an unreacted material or precipitates in the electrolyte at room temperature, and, accordingly, life or resistance characteristics of the secondary battery may be degraded.

Lithium Secondary Battery

Also, in the present invention, there is provided a lithium secondary battery including the non-aqueous electrolyte solution for a lithium secondary battery of the present invention.

In this case, the lithium secondary battery may be a high voltage lithium secondary battery operated at a high voltage of 4.45 V or more.

The lithium secondary battery including the non-aqueous electrolyte solution according to the present invention may exhibit excellent thermal stability by suppressing gas generation and cell swelling when it is stored at a high temperature after charged to a high voltage of 4.35 V or more.

The electrolyte for a lithium secondary battery of the present invention may be usefully used during the preparation of a lithium secondary battery.

Specifically, after an electrode assembly composed of a positive electrode, a negative electrode, and a separator disposed between the positive electrode and the negative electrode is prepared and the electrode assembly is accommodated in a battery case, the lithium secondary battery according to the present invention may be prepared by injecting an electrolyte for a lithium secondary battery. In this case, the lithium secondary battery may be prepared according to a conventional method of preparing a secondary battery except that the electrolyte for a lithium secondary battery according to the present invention is used.

(1) Positive Electrode

First, the positive electrode may be prepared by forming a positive electrode material mixture layer on a positive electrode collector. The positive electrode material mixture layer may be formed by coating the positive electrode collector with a positive electrode slurry including a positive electrode active material, a binder, a conductive agent, and a solvent, and then drying and rolling the coated positive electrode collector.

The positive electrode collector is not particularly limited so long as it has conductivity without causing adverse chemical changes in the battery, and, for example, stainless steel, aluminum, nickel, titanium, fired carbon, or aluminum or stainless steel that is surface-treated with one of carbon, nickel, titanium, silver, or the like may be used.

The positive electrode active material is a compound capable of reversibly intercalating and deintercalating lithium, wherein the positive electrode active material may specifically include a lithium composite metal oxide including lithium and at least one metal such as cobalt, manganese, nickel, or aluminum. Specifically, the lithium composite metal oxide may include lithium-manganese-based oxide (e.g., $LiMnO_2$, $LiMn_2O_4$, etc.), lithium-cobalt-based oxide (e.g., $LiCoO_2$, etc.), lithium-nickel-based oxide (e.g., $LiNiO_2$, etc.), lithium-nickel-manganese-based oxide (e.g., $LiNi_{1-Y}Mn_YO_2$ (where $0<Y<1$), $LiMn_{2-Z}Ni_ZO_4$ (where $0<Z<2$), etc.), lithium-nickel-cobalt-based oxide (e.g., $LiNi_{1-Y1}Co_{Y1}O_2$ (where $0<Y1<1$), lithium-manganese-cobalt-based oxide (e.g., $LiCo_{1-Y2}Mn_{Y2}O_2$ (where $0<Y2<1$), $LiMn_{2-Z1}Co_{Z1}O_4$ (where $0<Z1<2$) etc.), lithium-nickel-manganese-cobalt-based oxide (e.g., $Li(Ni_pCo_qMn_{r1})O_2$ (where $0<p<1$, $0<q<1$, $0<r1<1$, and $p+q+r1=1$) or $Li(Ni_{p1}Co_{q1}Mn_{r2})O_4$ (where $0<p1<2$, $0<q1<2$, $0<r2<2$, and $p1+q1+r2=2$), etc.), or lithium-nickel-cobalt-transition metal (M) oxide (e.g., $Li\ (Ni_{p2}Co_{q2}Mn_{r3}M_{s2})O_2$ (where M is selected from the group consisting of aluminum (Al), iron (Fe), vanadium (V), chromium (Cr), titanium (Ti), tantalum (Ta), magnesium (Mg), and molybdenum (Mo), and p2, q2, r3, and s2 are atomic fractions of each independent elements, wherein $0<p2<1$, $0<q2<1$, $0<r3<1$, $0<S2<1$, and $p2+q2+r3+S2=1$), etc.), and any one thereof or a compound of two or more thereof may be included.

Among these materials, in terms of the improvement of capacity characteristics and stability of the battery, the lithium composite metal oxide may include $LiCoO_2$, $LiMnO_2$, $LiNiO_2$, lithium nickel manganese cobalt oxide (e.g., $Li(Ni_{1/3}Mn_{1/3}Co_{1/3})O_2$, $Li\ (Ni_{0.6}Mn_{0.2}Co_{0.2})O_2$, $Li(Ni_{0.5}Mn_{0.3}Co_{0.2})O_2$, $Li(Ni_{0.7}Mn_{0.15}Co_{0.15})O_2$, or $Li(Ni_{0.8}Mn_{0.1}Co_{0.1})O_2$), or lithium nickel cobalt aluminum oxide (e.g., $LiNi_{0.8}Co_{0.15}Al_{0.05}O_2$, etc.).

The positive electrode active material may be included in an amount of 80 wt % to 99.5 wt %, for example, 85 wt % to 95 wt %, based on a total weight of solid content in the positive electrode slurry. In a case in which the amount of the positive electrode active material is 80 wt % or less, since energy density is reduced, capacity may be reduced.

Also, the binder is a component that assists in the binding between the active material and the conductive agent and in the binding with the current collector, wherein the binder is commonly added in an amount of 1 wt % to 30 wt % based on the total weight of the solid content in the positive electrode slurry. Examples of the binder may be polyvinylidene fluoride (PVDF), polyvinyl alcohol, carboxymethylcellulose (CMC), starch, hydroxypropylcellulose, regenerated cellulose, polyvinylpyrrolidone, tetrafluoroethylene, polyethylene, polypropylene, an ethylene-propylene-diene terpolymer (EPDM), a sulfonated EPDM, a styrene-butadiene rubber, a fluoro rubber, various copolymers, and the like.

Furthermore, any conductive agent may be used as the conductive agent without particular limitation so long as it has conductivity without causing adverse chemical changes in the battery, and, for example, a conductive material, such as: carbon powder such as carbon black, acetylene black, Ketjen black, channel black, furnace black, lamp black, or thermal black; graphite powder such as natural graphite with a well-developed crystal structure, artificial graphite, or graphite; conductive fibers such as carbon fibers or metal fibers; metal powder such as fluorocarbon powder, aluminum powder, and nickel powder; conductive whiskers such as zinc oxide whiskers and potassium titanate whiskers; conductive metal oxide such as titanium oxide; or polyphenylene derivatives, may be used.

In this case, the conductive agent may have an average particle diameter ($D_{50}$) of 10 μm or less, particularly 0.01 μm to 10 μm, and more particularly 0.01 μm to 1 μm.

The conductive agent is commonly added in an amount of 1 wt % to 30 wt % based on the total weight of the solid content in the positive electrode slurry.

Also, the solvent may include an organic solvent, such as N-methyl-2-pyrrolidone (NMP), and may be used in an amount such that desirable viscosity is obtained when the positive electrode active material as well as selectively the binder and the conductive agent are included. For example, the solvent may be included in an amount such that a concentration of the solid content in the slurry including the positive electrode active material as well as selectively the binder and the conductive agent is in a range of 10 wt % to 60 wt %, for example, 20 wt % to 50 wt %.

(2) Negative Electrode

The negative electrode may be prepared by forming a negative electrode material mixture layer on a negative electrode collector. The negative electrode material mixture layer may be formed by coating the negative electrode collector with a negative electrode slurry including a negative electrode active material, a binder, a conductive agent, and a solvent, and then drying and rolling the coated negative electrode collector.

The negative electrode collector generally has a thickness of 3 μm to 500 μm. The negative electrode collector is not particularly limited so long as it has high conductivity without causing adverse chemical changes in the battery, and, for example, copper, stainless steel, aluminum, nickel, titanium, fired carbon, copper or stainless steel that is surface-treated with one of carbon, nickel, titanium, silver, or the like, an aluminum-cadmium alloy, or the like may be used. Also, similar to the positive electrode collector, the negative electrode collector may have fine surface roughness to improve bonding strength with the negative electrode active material, and the negative electrode collector may be used in various shapes such as a film, a sheet, a foil, a net, a porous body, a foam body, a non-woven fabric body, and the like.

Furthermore, the negative electrode active material may include at least one selected from the group consisting of lithium metal, a carbon material capable of reversibly intercalating/deintercalating lithium ions, metal or an alloy of lithium and the metal, a metal composite oxide, a material which may be doped and undoped with lithium, and a transition metal oxide.

As the carbon material capable of reversibly intercalating/deintercalating lithium ions, a carbon-based negative electrode active material generally used in a lithium ion secondary battery may be used without particular limitation, and, as a typical example, crystalline carbon, amorphous carbon, or both thereof may be used. Examples of the crystalline carbon may be graphite such as irregular, planar, flaky, spherical, or fibrous natural graphite or artificial graphite, and examples of the amorphous carbon may be soft carbon (low-temperature sintered carbon) or hard carbon, mesophase pitch carbide, and fired cokes.

As the metal or the alloy of lithium and the metal, a metal selected from the group consisting of copper (Cu), nickel (Ni), sodium (Na), potassium (K), rubidium (Rb), cesium (Cs), francium (Fr), beryllium (Be), magnesium (Mg), calcium (Ca), strontium (Sr), silicon (Si), antimony (Sb), lead (Pb), indium (In), zinc (Zn), barium (Ba), radium (Ra), germanium (Ge), aluminum (Al), and tin (Sn), or an alloy of lithium and the metal may be used.

One selected from the group consisting of PbO, $PbO_2$, $Pb_2O_3$, $Pb_3O_4$, $Sb_2O_3$, $Sb_2O_4$, $Sb_2O_5$, GeO, $GeO_2$, $Bi_2O_3$, $Bi_2O_4$, $Bi_2O_5$, $Li_xFe_2O_3$ (0≤x≤1), $Li_xWO_2$ (0≤x≤1), and $Sn_xMe_{1-x}Me'_yO_z$ (Me: manganese (Mn), Fe, Pb, or Ge; Me': Al, boron (B), phosphorus (P), Si, Groups I, II and III elements of the periodic table, or halogen; 0<x≤1; 1≤y≤3; 1≤x≤8) may be used as the metal composite oxide.

The material, which may be doped and undoped with lithium, may include Si, $SiO_x$ (0<x≤2), a Si—Y alloy (where Y is an element selected from the group consisting of alkali metal, alkaline earth metal, a Group 13 element, a Group 14 element, transition metal, a rare earth element, and a combination thereof, and is not Si), Sn, $SnO_2$, and Sn—Y (where Y is an element selected from the group consisting of alkali metal, alkaline earth metal, a Group 13 element, a Group 14 element, transition metal, a rare earth element, and a combination thereof, and is not Sn), and a mixture of $SiO_2$ and at least one thereof may also be used. The element Y may be selected from the group consisting of Mg, Ca, Sr, Ba, Ra, scandium (Sc), yttrium (Y), Ti, zirconium (Zr), hafnium (Hf), rutherfordium (Rf), V, niobium (Nb), Ta, dubnium (db), Cr, Mo, tungsten (W), seaborgium (Sg), technetium (Tc), rhenium (Re), bohrium (Bh), Fe, Pb, ruthenium (Ru), osmium (Os), hassium (Hs), rhodium (Rh), iridium (Ir), palladium (Pd), platinum (Pt), Cu, silver (Ag), gold (Au), Zn, cadmium (Cd), B, Al, gallium (Ga), Sn, In, Ge, P, arsenic (As), Sb, bismuth (Bi), sulfur (S), selenium (Se), tellurium (Te), polonium (Po), and a combination thereof.

The transition metal oxide may include lithium-containing titanium composite oxide (LTO), vanadium oxide, and lithium vanadium oxide.

The negative electrode active material may be included in an amount of 80 wt % to 99 wt % based on a total weight of solid content in the negative electrode slurry.

The binder is a component that assists in the binding between the conductive agent, the active material, and the current collector, wherein the binder is commonly added in an amount of 1 wt % to 30 wt % based on the total weight of the solid content in the negative electrode slurry. Examples of the binder may be polyvinylidene fluoride (PVDF), polyvinyl alcohol, carboxymethylcellulose (CMC), starch, hydroxypropylcellulose, regenerated cellulose, polyvinylpyrrolidone, tetrafluoroethylene, polyethylene, polypropylene, an ethylene-propylene-diene polymer (EPDM), a sulfonated EPDM, a styrene-butadiene rubber, a fluoro rubber, and various copolymers thereof.

The conductive agent is a component for further improving the conductivity of the negative electrode active material, wherein the conductive agent may be added in an amount of 1 wt % to 20 wt % based on the total weight of the solid content in the negative electrode slurry. Any conductive agent may be used without particular limitation so long as it has conductivity without causing adverse chemical changes in the battery, and the same conductive agent as that included in the positive electrode active material may be used. For example, a conductive material, such as: graphite such as natural graphite or artificial graphite; carbon black such as acetylene black, Ketjen black, channel black, furnace black, lamp black, and thermal black; conductive fibers such as carbon fibers and metal fibers; metal powder such as fluorocarbon powder, aluminum powder, and nickel powder; conductive whiskers such as zinc oxide whiskers and potassium titanate whiskers; conductive metal oxide such as titanium oxide; or polyphenylene derivatives, may be used.

The solvent may include water or an organic solvent, such as NMP and alcohol, and may be used in an amount such that desirable viscosity is obtained when the negative electrode active material as well as selectively the binder and the conductive agent are included. For example, the solvent may be included in an amount such that a concentration of the solid content in the negative electrode slurry including the negative electrode active material as well as selectively the binder and the conductive agent is in a range of 50 wt % to 80 wt %, for example, 50 wt % to 75 wt %.

(3) Separator

Also, the separator plays a role in blocking an internal short circuit between both electrodes and being impregnated with the electrolyte, wherein, after mixing a polymer resin, a filler, and a solvent to prepare a separator composition, the separator composition is directly coated on the electrode and dried to form a separator film, or, after the separator composition is cast on a support and dried, the separator may be prepared by laminating a separator film peeled from the support on the electrode.

A typically used porous polymer film, for example, a porous polymer film prepared from a polyolefin-based polymer, such as an ethylene homopolymer, a propylene homopolymer, an ethylene/butene copolymer, an ethylene/hexene copolymer, and an ethylene/methacrylate copolymer, may be used alone or in a lamination therewith as the separator. Also, a typical porous nonwoven fabric, for example, a nonwoven fabric formed of high melting point glass fibers or polyethylene terephthalate fibers may be used, but the present invention is not limited thereto.

In this case, the porous separator may generally have a pore diameter of 0.01 μm to 50 μm and a porosity of 5% to 95%. Also, the porous separator may generally have a thickness of 5 μm to 300 μm.

A shape of the lithium secondary battery of the present invention is not particularly limited, but the lithium secondary battery may have various shapes, such as a cylindrical shape, a prismatic shape, a pouch shape, or a coin shape, depending on purposes. The lithium secondary battery according to the embodiment of the present invention may be a pouch type secondary battery.

Hereinafter, the present invention will be described in more detail according to examples. However, the invention may be embodied in many different forms and should not be construed as being limited to the embodiments set forth herein. Rather, these example embodiments are provided so that this description will be thorough and complete, and will fully convey the scope of the present invention to those skilled in the art.

EXAMPLES

Example 1

(Non-Aqueous Electrolyte Solution Preparation)

A non-aqueous electrolyte solution of the present invention was prepared by adding 2 g of the compound represented by Formula 1a, as an additive, to 98 g of a non-aqueous organic solvent (ethylene carbonate (EC):propyl propionate (PP)=volume ratio of 30:70) in which 1.2 M $LiPF_6$ was dissolved.

(Secondary Battery Preparation)

Lithium cobalt composite oxide ($LiCoO_2$) as positive electrode active material particles, carbon black as a conductive agent, and polyvinylidene fluoride (PVDF), as a binder, were added to N-methyl-2-pyrrolidone (NMP), as a solvent, in a weight ratio of 90:5:5 to prepare a positive electrode active material slurry (solid content 45 wt %). A 100 μm thick positive electrode collector (Al thin film) was coated with the positive electrode active material slurry, dried, and roll-pressed to prepare a positive electrode.

Next, natural graphite, as a negative electrode active material, PVDF as a binder, and carbon black, as a conductive agent, were added to NMP, as a solvent, in a weight ratio of 95:2:3 to prepare a negative electrode active material slurry (solid content 75 wt %). A 90 μm thick negative electrode collector (Cu thin film) was coated with the negative electrode active material slurry, dried, and roll-pressed to prepare a negative electrode.

After an electrode assembly was prepared by a typical method of sequentially stacking a polyethylene porous film with the above-prepared positive electrode and negative electrode, the electrode assembly was accommodated in a case, and the above-prepared non-aqueous electrolyte solution was injected to prepare a lithium secondary battery.

Example 2

A non-aqueous electrolyte solution for a lithium secondary battery and a lithium secondary battery including the same were prepared in the same manner as in Example 1 except that the compound of Formula 1b, instead of the compound of Formula 1a, was included as an additive during the preparation of the non-aqueous electrolyte solution.

Example 3

A non-aqueous electrolyte solution for a lithium secondary battery and a lithium secondary battery including the same were prepared in the same manner as in Example 1 except that the compound of Formula 1c, instead of the compound of Formula 1a, was included as an additive during the preparation of the non-aqueous electrolyte solution.

Example 4

A non-aqueous electrolyte solution for a lithium secondary battery and a lithium secondary battery including the same were prepared in the same manner as in Example 1 except that 0.1 g of the compound of Formula 1a was included in 99.9 g of a non-aqueous organic solvent (ethylene carbonate (EC):propyl propionate (PP)=volume ratio of 30:70), in which 1.2 M $LiPF_6$ was dissolved, during the preparation of the non-aqueous electrolyte solution.

Example 5

A non-aqueous electrolyte solution for a lithium secondary battery and a lithium secondary battery including the same were prepared in the same manner as in Example 1 except that 10 g of the compound of Formula 1a was included in 90 g of a non-aqueous organic solvent (ethylene carbonate (EC):propyl propionate (PP)=volume ratio of 30:70), in which 1.2 M $LiPF_6$ was dissolved, during the preparation of the non-aqueous electrolyte solution.

Example 6

A non-aqueous electrolyte solution for a lithium secondary battery and a lithium secondary battery including the same were prepared in the same manner as in Example 1 except that 0.01 g of the compound of Formula 1b was included in 99.99 g of a non-aqueous organic solvent (ethylene carbonate (EC):propyl propionate (PP)=volume ratio of 30:70), in which 1.2 M $LiPF_6$ was dissolved, during the preparation of the non-aqueous electrolyte solution.

Example 7

A non-aqueous electrolyte solution for a lithium secondary battery and a lithium secondary battery including the same were prepared in the same manner as in Example 1 except that 7 g of the compound of Formula 1b was included in 93 g of a non-aqueous organic solvent (EC:propylene carbonate (PC):PP=volume ratio of 20:10:70), in which 1.2 M $LiPF_6$ was dissolved, during the preparation of the non-aqueous electrolyte solution.

Example 8

A non-aqueous electrolyte solution for a lithium secondary battery and a lithium secondary battery including the same were prepared in the same manner as in Example 1 except that 7 g of the compound of Formula 1a was included in 93 g of a non-aqueous organic solvent (EC:PP=volume ratio of 20:80), in which 1.2 M $LiPF_6$ was dissolved, during the preparation of the non-aqueous electrolyte solution.

Example 9

A non-aqueous electrolyte solution for a lithium secondary battery and a lithium secondary battery including the same were prepared in the same manner as in Example 1 except that 7 g of the compound of Formula 1a was included in 93 g of a non-aqueous organic solvent (EC:PP=volume ratio of 40:60), in which 1.2 M $LiPF_6$ was dissolved, during the preparation of the non-aqueous electrolyte solution.

Example 10

A non-aqueous electrolyte solution for a lithium secondary battery and a lithium secondary battery including the same were prepared in the same manner as in Example 1 except that 13 g of the compound of Formula 1a was included in 87 g of a non-aqueous organic solvent (ethylene carbonate (EC):propyl propionate (PP)=volume ratio of 30:70), in which 1.2 M $LiPF_6$ was dissolved, during the preparation of the non-aqueous electrolyte solution.

Example 11

A non-aqueous electrolyte solution for a lithium secondary battery and a lithium secondary battery including the same were prepared in the same manner as in Example 1 except that 0.009 g of the compound of Formula 1a was included in 99.991 g of a non-aqueous organic solvent (EC:PC:PP=volume ratio of 20:10:70), in which 1.2 M $LiPF_6$ was dissolved, during the preparation of the non-aqueous electrolyte solution.

Comparative Example 1

A non-aqueous electrolyte solution for a lithium secondary battery and a lithium secondary battery including the same were prepared in the same manner as in Example 1 except that the compound of Formula 1a was not included as an additive during the preparation of the non-aqueous electrolyte solution.

Comparative Example 2

A non-aqueous electrolyte solution for a lithium secondary battery and a lithium secondary battery including the same were prepared in the same manner as in Example 1 except that a compound of the following Formula 2, instead of the compound of Formula 1a, was included as an additive during the preparation of the non-aqueous electrolyte solution.

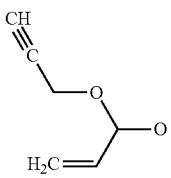

[Formula 2]

Comparative Example 3

A non-aqueous electrolyte solution for a lithium secondary battery and a lithium secondary battery including the same were prepared in the same manner as in Example 1 except that a compound of the following Formula 3, instead of the compound of Formula 1a, was included as an additive during the preparation of the non-aqueous electrolyte solution.

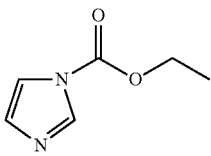

[Formula 3]

Comparative Example 4

A non-aqueous electrolyte solution for a lithium secondary battery and a lithium secondary battery including the same were prepared in the same manner as in Example 1 except that 2 g of the compound of Formula 1a was included in 98 g of a non-aqueous organic solvent (EC:EMC=volume ratio of 30:70), in which 1.2 M $LiPF_6$ was dissolved, during the preparation of the non-aqueous electrolyte solution.

EXPERIMENTAL EXAMPLES

Experimental Example 1: Evaluation of Cycle Life Characteristics

Each of the lithium secondary batteries prepared in Examples 1 to 11 and the lithium secondary batteries prepared in Comparative Examples 1 to 4 was charged at 1.0 C/4.45 V to 4.45 V/112 mA under a constant current/constant voltage (CC/CV) condition at 45° C. and discharged at 1.0 C to 3.0 V.

The above charging and discharging were set as one cycle, and 200 cycles of charging and discharging were performed.

In this case, capacity after a first cycle and capacity after a $200^{th}$ cycle were measured using PNE-0506 charge/discharge equipment (manufacturer: PNE SOLUTION Co., Ltd., 5 V, 6 A), and capacity retention was measured by substituting the capacities into the following Equation (1). The results thereof are listed in Table 1 below. In addition, the results of cycle life characteristics of the lithium secondary batteries prepared in Examples 1 to 5, 10, and 11 and the secondary batteries prepared in Comparative Examples 1 to 3 are shown in the FIGURE below.

$$\text{capacity retention (\%)} = (\text{capacity after 200 cycles}/\text{capacity after one cycle}) \times 100 \quad \text{Equation (1)}$$

TABLE 1

| | Non-aqueous organic solvent | | Additive | | Capacity |
|---|---|---|---|---|---|
| | Organic solvent (volume ratio) | Addition amount (g) | Formula | Addition amount (g) | retention after 200 cycles (%) |
| Example 1 | EC:PP = 30:70 | 98 | 1a | 2 | 89 |
| Example 2 | EC:PP = 30:70 | 98 | 1b | 2 | 83 |
| Example 3 | EC:PP = 30:70 | 98 | 1c | 2 | 84 |
| Example 4 | EC:PP = 30:70 | 99.9 | 1a | 0.1 | 81 |
| Example 5 | EC:PP = 30:70 | 90 | 1a | 10 | 82 |
| Example 6 | EC:PP = 30:70 | 99.99 | 1b | 0.01 | 80 |
| Example 7 | EC:PC:PP = 20:10:70 | 93 | 1b | 7 | 82 |
| Example 8 | EC:PP = 20:80 | 93 | 1a | 7 | 85 |
| Example 9 | EC:PP = 40:60 | 93 | 1a | 7 | 86 |
| Example 10 | EC:PP = 30:70 | 87 | 1a | 13 | 80 |
| Example 11 | EC:PC:PP = 20:10:70 | 99.991 | 1a | 0.009 | 79 |
| Comparative Example 1 | EC:PP = 30:70 | 100 | — | — | 70 |
| Comparative Example 2 | EC:PP = 30:70 | 98 | 2 | 2 | 72 |
| Comparative Example 3 | EC:PP = 30:70 | 98 | 3 | 2 | 76 |
| Comparative Example 4 | EC:EMC = 30:70 | 98 | 1a | 2 | 81 |

As illustrated in Table 1 and the FIGURE, with respect to the lithium secondary batteries of Examples 1 to 11 which included the non-aqueous electrolyte solutions including the compound represented by Formula 1 of the present invention as an additive, cycle life characteristics was 79% or more, but it may be understood that cycle life characteristics of the lithium secondary batteries of Comparative Examples 1 to 3 was lower at 76% or less.

Referring to Table 1, with respect to the lithium secondary battery of Comparative Example 4 which included the non-aqueous electrolyte solution including ethyl methyl carbonate, instead of propyl propionate, as the non-aqueous solvent, it may be understood that cycle life characteristics were equivalent to those of the lithium secondary battery of the present invention.

Experimental Example 2: Evaluation of Thickness and Resistance Increase Rate Each of the lithium secondary batteries prepared in Examples 1 to 11 and the lithium secondary batteries prepared in Comparative Examples 1 to 4 was charged at a 0.7 C rate to 4.45 V under a constant current/constant voltage condition, cut-off charged at 0.05 C, and discharged at 0.5 C to a voltage of 3.0 V. After checking initial capacity, each of the lithium secondary batteries was charged at a 0.7 C rate to 4.45 V under a constant current/constant voltage condition, cut-off charged at 0.05 C, and discharged at a 0.5 C rate to a voltage of 3 V.

Subsequently, an initial thickness of each of the lithium secondary batteries was measured using a plate thickness gauge equipped with a 600 g weight. Also, AC resistance was measured using a VMP3 model by Bio-logic Science Instruments.

Next, each of the lithium secondary batteries was stored at 85° C. for 8 hours and then cooled, and increased thicknesses of the lithium secondary batteries prepared in Examples 1 to 11 and the lithium secondary batteries of Comparative Examples 1 to 4 and resistances of the lithium secondary batteries of Examples 1 to 11 and the lithium secondary batteries of Comparative Examples 1 to 4 were respectively measured, and the results thereof are presented in Table 2 below.

In this case, a thickness increase rate (%) of the battery was calculated by using the following Equation (2).

Also, a resistance increase rate (%) of the battery was calculated by using the following Equation (3).

thickness increase rate (%)={(thickness after high-temperature storage initial thickness)/initial thickness}×100    Equation (2)

resistance increase rate (%)={(resistance after high-temperature storage/initial resistance)×100}−100    Equation (3)

may be understood that a resistance increase rate after high-temperature storage was 53.0% which was inferior to those of the lithium secondary batteries of Examples 1 to 9.

With respect to the secondary battery of Example 11 which included the non-aqueous electrolyte solution containing a small amount of the additive, since an effect of the additive in the electrolyte solution was insignificant, a thickness increase rate was equivalent to those of the secondary batteries of Examples 1 to 9, but a resistance increase rate after high-temperature storage was 53.7%, wherein it may be understood that the resistance increase rate after high-temperature storage was inferior to those of the secondary batteries of Examples 1 to 9.

With respect to the secondary battery of Comparative Example 4 which included the non-aqueous electrolyte solution not including propyl propionate as the non-aqueous solvent, a resistance increase rate after high-temperature storage was 58.3% and, since an amount of gas generated was increased, a thickness increase rate after high-temperature storage was 5.08%, wherein it may be understood that the resistance increase rate and thickness increase rate after high-temperature storage was increased in comparison to those of the lithium secondary batteries of Examples 1 to 9.

TABLE 2

| | Non-aqueous organic solvent | | Additive | | Thickness increase rate after high-temperature storage (%) | Resistance increase rate after high-temperature storage (%) |
|---|---|---|---|---|---|---|
| | Organic solvent (volume ratio) | Addition amount (g) | Formula | Addition amount (g) | | |
| Example 1 | EC:PP = 30:70 | 98 | 1a | 2 | 3.41 | 42.1 |
| Example 2 | EC:PP = 30:70 | 98 | 1b | 2 | 3.49 | 49.4 |
| Example 3 | EC:PP = 30:70 | 98 | 1c | 2 | 4.25 | 44.3 |
| Example 4 | EC:PP = 30:70 | 99.9 | 1a | 0.1 | 3.57 | 50.4 |
| Example 5 | EC:PP = 30:70 | 90 | 1a | 10 | 4.60 | 51.1 |
| Example 6 | EC:PP = 30:70 | 99.99 | 1b | 0.01 | 3.63 | 51.8 |
| Example 7 | EC:PC:PP = 20:10:70 | 93 | 1b | 7 | 3.70 | 47.6 |
| Example 8 | EC:PP = 20:80 | 93 | 1a | 7 | 3.78 | 43.4 |
| Example 9 | EC:PP = 40:60 | 93 | 1a | 7 | 4.81 | 52.7 |
| Example 10 | EC:PP = 30:70 | 87 | 1a | 13 | 4.63 | 53.0 |
| Example 11 | EC:PC:PP = 20:10:70 | 99.991 | 1a | 0.009 | 4.45 | 53.7 |
| Comparative Example 1 | EC:PP = 30:70 | 100 | — | — | 4.82 | 61.1 |
| Comparative Example 2 | EC:PP = 30:70 | 98 | 2 | 2 | — | 58.3 |
| Comparative Example 3 | EC:PP = 30:70 | 98 | 3 | 2 | — | 55.0 |
| Comparative Example 4 | EC:EMC = 30:70 | 98 | 1a | 2 | 5.08 | 58.3 |

Referring to Table 2, with respect to the lithium secondary batteries of Examples 1 to 9 which included the non-aqueous electrolyte solutions including the compound represented by Formula 1 of the present invention as an additive, it may be understood that thickness increase rates after high-temperature storage were mostly 4.81% or less and resistance increase rates after high-temperature storage were mostly 52.7% or less.

A thickness increase rate of the secondary battery of Example 10, which included the non-aqueous electrolyte solution containing an excessive amount of the additive, was 4.63% which was equivalent to those of the lithium secondary batteries of Examples 1 to 9, but, since a life capacity degradation phenomenon occurred due to an increase in resistance caused by the excessive amount of the additive, it Also, the secondary battery of Comparative Example 1 including the non-aqueous electrolyte solution without the additive of the present invention had a thickness increase rate after high-temperature storage of 4.82% and a resistance increase rate after high-temperature storage of 61.1%, wherein it may be understood that these were significantly inferior to those of the secondary batteries of Examples 1 to 9.

Resistance increase rates after high-temperature storage of the secondary batteries of Comparative Examples 2 an 3 respectively including the additives of Formulae 2 and 3 instead of the additive of the present invention were 58.3% and 55.0%, respectively, wherein it may be understood that the resistance increase rates after high-temperature storage were significantly inferior to those of the secondary batteries of Examples 1 to 9.

Experimental Example 3: Metal Dissolution Analysis

Each of the secondary batteries of Examples 1, 4, 5, 10, and 11 and the secondary batteries of Comparative Examples 1 to 3 was charged at 0.33 C/4.25 V under a constant current/constant voltage (CC/CV) condition at 25° C. to 4.2 V/38 mA at 1 C and then discharged at a constant current of 3 C for 10 seconds to 2.5 V at a state of charge (SOC) of 50%.

The above charging and discharging were set as one cycle, and 500 cycles of charging and discharging were performed.

A concentration of total metal dissolved in the electrolyte solution was measured using an inductively coupled plasma optical emission spectrophotometer (ICP-OES). An amount of the metal measured using ICP analysis is presented in Table 3 below.

Next, after each of the secondary batteries was stored at a SOC of 50% for 2 weeks at 60° C., a concentration of total metal dissolved in the electrolyte solution after high-temperature storage was measured using the ICP-OES. An amount of the metal measured using ICP analysis is presented in Table 3 below.

TABLE 3

| | Non-aqueous organic solvent | | Additive | | Amount of metal dissolved after high-temperature storage (ppm) | Amount of metal dissolved after 500 cycles (ppm) |
| --- | --- | --- | --- | --- | --- | --- |
| | Organic solvent (volume ratio) | Addition amount (g) | Formula | Addition amount (g) | | |
| Example 1 | EC:PP = 30:70 | 98 | 1a | 2 | 1510 | 1310 |
| Example 4 | EC:PP = 30:70 | 99.9 | 1a | 0.1 | 1560 | 1450 |
| Example 5 | EC:PP = 30:70 | 90 | 1a | 10 | 1310 | 1210 |
| Example 10 | EC:PP = 30:70 | 87 | 1a | 13 | 1320 | 1200 |
| Example 11 | EC:PP = 30:70 | 99.991 | 1a | 0.009 | 1750 | 1650 |
| Comparative Example 1 | EC:PP = 30:70 | 100 | — | — | 3510 | 4980 |
| Comparative Example 2 | EC:PP = 30:70 | 98 | 2 | 2 | 2850 | 3300 |
| Comparative Example 3 | EC:PP = 30:70 | 98 | 3 | 2 | 3160 | 4410 |

As illustrated in Table 3, with the secondary batteries of Examples 1, 4, 5, and 10 which included the non-aqueous electrolyte solutions including the compound represented by Formula 1 of the present invention as an additive, it may be understood that amounts of metal dissolved after 500 cycles were 1,450 ppm or less, and amounts of metal dissolved after high-temperature storage were suppressed to 1,560 ppm or less.

With respect to the secondary battery of Example 11 which included the non-aqueous electrolyte solution containing a small amount of the additive, since the effect of the additive in the electrolyte solution was insignificant, an amount of metal dissolved after 500 cycles was 1,650 ppm, and a amount of metal dissolved after high-temperature storage was 1,750 ppm, wherein it may be understood that these were significantly increased in comparison to those of the secondary batteries of Examples 1, 4, 5, and 10.

Also, with respect to the secondary battery of Comparative Example 1 which included the non-aqueous electrolyte solution not containing the compound represented by Formula 1 as an additive, it may be confirmed that a metal dissolution amount was significantly increased in comparison to those of the secondary batteries of Examples 1, 4, 5, and 10.

Furthermore, since the secondary battery of Comparative Example 2, which included the non-aqueous electrolyte solution containing the compound represented by Formula 2 as an additive, included a metal dissolution inhibiting functional group, it may be understood that a metal dissolution amount was slightly reduced in comparison to that of Comparative Example 1 including the non-aqueous electrolyte solution without an additive, but the metal dissolution amount was significantly inferior to those of the secondary batteries of Examples 1, 4, 5, and 10.

Also, since the secondary battery of Comparative Example 3, which included the non-aqueous electrolyte solution containing the compound represented by Formula 3 as an additive, had an insignificant metal dissolution suppression effect, it may be confirmed that a metal dissolution amount was similar to that of the secondary battery of Comparative Example 1.

The invention claimed is:

1. A non-aqueous electrolyte solution for a lithium secondary battery, the non-aqueous electrolyte solution comprising:

a lithium salt, a non-aqueous solvent including a carbonate-based solvent and propyl propionate, and a compound represented by Formula 1:

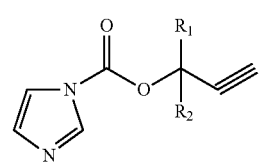

[Formula 1]

wherein, in Formula 1, $R_1$ and $R_2$ are each independently hydrogen or a substituted or unsubstituted alkyl group having 1 to 6 carbon atoms.

2. The non-aqueous electrolyte solution for a lithium secondary battery of claim 1, wherein the non-aqueous solvent comprises the carbonate-based solvent and the propyl propionate in a weight ratio of 2:8 to 4:6.

3. The non-aqueous electrolyte solution for a lithium secondary battery of claim 1, wherein the carbonate-based solvent is ethylene carbonate.

4. The non-aqueous electrolyte solution for a lithium secondary battery of claim 1, wherein the non-aqueous solvent further comprises ethyl propionate.

5. The non-aqueous electrolyte solution for a lithium secondary battery of claim 1, wherein the compound represented by Formula 1 is selected from the group consisting of compounds represented by Formulae 1a to 1c:

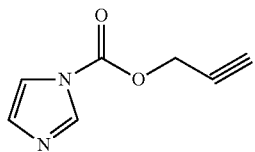

[Formula 1a]

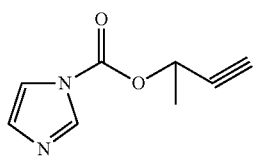

[Formula 1b]

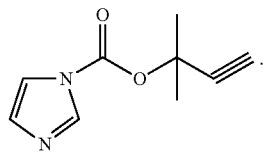

[Formula 1c]

6. The non-aqueous electrolyte solution for a lithium secondary battery of claim 5, wherein the compound represented by Formula 1 is selected from the group consisting of the compounds represented by Formulae 1b and 1c.

7. The non-aqueous electrolyte solution for a lithium secondary battery of claim 1, wherein the compound represented by Formula 1 is included in an amount of 0.01 wt % to 11.5 wt % based on a total weight of the non-aqueous electrolyte solution.

8. The non-aqueous electrolyte solution for a lithium secondary battery of claim 1, wherein the compound represented by Formula 1 is included in an amount of 0.1 wt % to 10 wt % based on a total weight of the non-aqueous electrolyte solution.

9. A lithium secondary battery comprising the non-aqueous electrolyte solution of claim 1.

* * * * *